United States Patent
Al-Daous (10) Patent No.: US 10,413,887 B1
(45) Date of Patent: Sep. 17, 2019

(54) CATALYST SYSTEMS USEFUL IN DEHYDROGENATION REACTIONS

(71) Applicant: Saudi Arabian Oil Company, Dhahran (SA)

(72) Inventor: Mohammed Abdulmajeed Al-Daous, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/910,291

(22) Filed: Mar. 2, 2018

(51) Int. Cl.
| | |
|---|---|
| *B01J 29/06* | (2006.01) |
| *B01J 23/58* | (2006.01) |
| *B01J 29/70* | (2006.01) |
| *B01J 35/00* | (2006.01) |
| *B01J 37/02* | (2006.01) |
| *B01J 37/08* | (2006.01) |
| *B01J 37/30* | (2006.01) |
| *C07C 5/333* | (2006.01) |
| *B01J 37/00* | (2006.01) |
| *B01J 29/035* | (2006.01) |
| *B01J 29/44* | (2006.01) |
| *B01J 37/16* | (2006.01) |
| *B01J 29/03* | (2006.01) |
| *C01B 39/38* | (2006.01) |
| *C01B 39/06* | (2006.01) |
| *C01B 39/02* | (2006.01) |

(52) U.S. Cl.
CPC .............. *B01J 23/58* (2013.01); *B01J 29/03* (2013.01); *B01J 29/0354* (2013.01); *B01J 29/44* (2013.01); *B01J 29/7049* (2013.01); *B01J 35/0006* (2013.01); *B01J 37/0009* (2013.01); *B01J 37/0201* (2013.01); *B01J 37/0215* (2013.01); *B01J 37/088* (2013.01); *B01J 37/16* (2013.01); *B01J 37/30* (2013.01); *C01B 39/02* (2013.01); *C01B 39/026* (2013.01); *C01B 39/06* (2013.01); *C01B 39/38* (2013.01); *C07C 5/3337* (2013.01); *B01J 2229/183* (2013.01); *B01J 2229/186* (2013.01); *B01J 2229/38* (2013.01); *C07C 2523/58* (2013.01); *C07C 2529/04* (2013.01)

(58) Field of Classification Search
CPC .... B01L 29/063; B01L 29/0354; B01L 29/44; B01L 37/0201; B01L 37/16; B01L 2229/183; B01L 2229/186; C01B 39/02; C01B 39/026; C01B 39/06; C01B 39/38

USPC ..... 502/60, 74, 77, 243, 250, 253, 258, 261, 502/262; 423/713
See application file for complete search history.

(56) References Cited

U.S. PATENT DOCUMENTS

| | | |
|---|---|---|
| 4,210,769 A | 7/1980 | Antos |
| 4,438,288 A | 3/1984 | Imai et al. |
| 4,665,267 A | 5/1987 | Barri |
| 4,962,266 A | 10/1990 | Shum |
| 5,126,502 A | 6/1992 | Barri et al. |
| 5,137,706 A | 8/1992 | Annen et al. |
| 5,208,201 A | 5/1993 | Barri et al. |
| 2006/0138026 A1 | 6/2006 | Chen et al. |

FOREIGN PATENT DOCUMENTS

EP 0 351 067 A1 6/1989

OTHER PUBLICATIONS

Li, et al., Pt/[Fe]ZSM-5 modified by Na and Cs cations: an active and selective catalyst for dehydrogenation of n-alkanes to n-alkenes, Chem. Commun. (2008), pp. 594-596.
International Search Report and Written Opinion pertaining to International Application No. PCT/US2018/037453.
Inui, et al., Effective Conversion of Paraffins to Aromatics on Pt Ion-Exchanged Ga- and Zn-Silicates, Studies in Surface Science and Catalysis, vol. 60, Jan. 1, 1988, pp. 487-494, Tokyo, Japan.
Ball, et al., Zinc and Aluminum Substitutions in MFI-Structures; Synthesis, Characterisation and Catalysis, Studies in Surface Science and Catalysis, vol. 28, Jan. 1, 1986, pp. 951-956, Tokyo, Japan.
Office Action dated Dec. 14, 2018 pertaining to U.S. Appl. No. 16/139,657, filed Sep. 24, 2018, 13 pgs.
Office Action dated Nov. 8, 2018 pertaining to U.S. Appl. No. 16/139,702, filed Sep. 24, 2018, 12 pgs.
Notice of Allowance and Fee(s) Due dated Mar. 27, 2019 pertaining to U.S. Appl. No. 16/139,657, filed Sep. 24, 2018, 20 pgs.
Final Office Action dated May 16, 2019 pertaining to U.S. Appl. No. 16/139,702, filed Sep. 24, 2018, 24 pgs.

*Primary Examiner* — Elizabeth D Wood
(74) *Attorney, Agent, or Firm* — Dinsmore and Shohl, LLP (57) ABSTRACT

The present disclosure relates to catalyst systems which may be useful for the dehydrogenation of hydrocarbons. According to one or more embodiments, the catalyst systems may include a zincosilicate support material, one or more alkali or alkaline earth metals, and one or more platinum group metals. The zincosilicate support material may include an MFI framework type structure incorporating at least silicon and zinc. The present disclosure also relates to methods for the production of such catalyst systems as well as methods for the use of such catalyst systems for the dehydration of hydrocarbons.

9 Claims, 1 Drawing Sheet

CATALYST SYSTEMS USEFUL IN DEHYDROGENATION REACTIONS

BACKGROUND

Field

Embodiments of the present disclosure generally relate to catalyst systems that may be used in dehydrogenation reactions and, more specifically, relate to catalyst systems, chemical reaction systems, and methods which may be utilized for hydrocarbon dehydrogenation.

Technical Background

Dehydrogenation is a chemical reaction that involves the removal of hydrogen from an organic hydrocarbon molecule. Dehydrogenation is an important reaction because it converts species such as alkanes, which are relatively inert and thus low-valued, to olefins, which are more reactive and thus generally more valuable. For example, dehydrogenation of paraffins and olefins may result in valuable products, such as when n-pentane or isopentene are converted to pentene and isoprene, respectively. Additionally, alkenes and alkadienes are valuable precursors for the production of aldehydes, alcohols, polymers, and aromatics.

Such dehydrogenation reactions may utilize chromium (III) oxide as a catalyst 500° C. However, catalysts with greater stability may be more efficient, or catalysts with better selectivity may be desired in industry for hydrocarbon dehydrogenation.

SUMMARY

Accordingly, there is a continual need for new catalysts which are well suited for the dehydrogenation of hydrocarbons, such as alkanes, with high selectivity for linear alkenes. The present disclosure relates to catalyst systems which may be utilized for dehydrogenation of at least alkanes, as well as the processes and systems which incorporate such presently described catalyst systems. The catalyst systems described presently may include a zincosilicate support that comprises an MFI framework type. Additionally, the catalyst systems may include alkali or alkaline earth metals, and may additionally include one or more platinum group metal catalysts. While the catalyst systems described in this disclosure are not necessarily limited in functionality, they may be catalytically active for hydrogenating alkanes, such as normal alkanes comprising from 2 to 10 carbon atoms (C2-C10 n-alkanes).

According to an embodiment described in the present disclosure, a catalyst system may be useful for the dehydrogenation of hydrocarbons. The catalyst system may comprise a zincosilicate support material, one or more alkali or alkaline earth metals, and one or more platinum group metals. The zincosilicate support material may comprise an MFI framework type structure incorporating at least silicon and zinc.

According to another embodiment described in the present disclosure, a catalyst system may be made by a method which may comprise introducing one or more alkali or alkaline earth metals to a zincosilicate support material. The method may further comprise introducing one or more platinum group metals to the zincosilicate support material. The zincosilicate support material may comprise an MFI framework type structure incorporating at least silicon and zinc.

According to yet another embodiment described in the present disclosure, one or more reactant hydrocarbons may be dehydrogenated by a method which may comprise contacting the one or more reactant hydrocarbons with a catalyst system to dehydrogenate at least a portion of the reactant hydrocarbons. The catalyst system may comprise a zincosilicate support material, one or more alkali or alkaline earth metals, and one or more platinum group metals. The zincosilicate support material may comprise an MFI framework type structure incorporating at least silicon and zinc.

Additional features and advantages of the embodiments described herein will be set forth in the detailed description which follows, and in part will be readily apparent to those skilled in the art from that description or recognized by practicing the embodiments described herein, including the detailed description which follows, and the claims.

BRIEF DESCRIPTION OF THE DRAWINGS

The following detailed description of specific embodiments of the present disclosure can be best understood when read in conjunction with the following drawings, where like structure is indicated with like reference numerals and in which.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to catalyst systems which include zincosilicate supported platinum group catalysts active in the dehydrogenation of alkanes, which may have particularly high selectivity for dehydrogenating n-alkanes (that is, "normal" or "linear" alkanes) to the corresponding linear alkenes or alkadienes. According to one or more embodiments, and without being bound by theory, the enhanced selectivity for linear alkene formation may be achieved by inhibiting skeletal isomerization and cracking side reactions on the catalyst through ion-exchanging the relatively weak acid sites on the zincosilicate support with one or more alkali or alkaline earth metals (such as, but not limited to, sodium (Na), potassium (K), or cesium (Cs)). In additional embodiments, ion-exchange with cesium or potassium may also impart the catalyst with additional stability against steaming, thereby enabling the use of steam as diluent in a feed stream. According to one or more additional embodiments, the addition of relatively small amounts of hydrogen (for example 5 percent by volume (vol. %) to 30 vol. %) to the diluent gas stream may enhance catalytic activity in at least C4 to C6 alkane dehydrogenation, may increase catalytic selectivity for linear alkenes and dienes in the product, and may further improve catalytic stability.

It should be understood that, as described herein, "catalyst systems" refer to materials which are catalytically active and may comprise a support material and one or more catalytically active materials, sometimes referred to as "the catalyst." For example, in the presently described catalyst systems, a zincosilicate may serve as the catalyst support and a platinum group metal may serve as the catalyst. However, it should be understood that the support material may be catalytically active, and that the catalyst system (including the support and the additional material or materials) may be referred to simply as a "catalyst" in some portions of this disclosure as would be understood by one skilled in the art.

The catalyst systems presently described may be utilized for the dehydrogenation of alkanes, such as n-pentanes, to produce hydrocarbons comprising double carbon bond moieties, such as n-pentenes (for example, 1-pentene, 2-cis-pentene, and 2-trans-pentene) with relatively high selectivity for such conversion. In additional embodiments, the presently described catalyst systems may be utilized for the dehydrogenation of C2-C10 alkanes (such as C2, C3, C4, C5, C6, C7, C8, C9, or C10 branched or straight chained alkanes). As such, the catalyst systems described herein may be sometimes referred to as "dehydrogenation catalysts" or "dehydrogenation catalyst systems."

The present disclosure also relates to methods for producing such catalyst systems, as well as the properties and structure of the produced catalyst systems. As used in this disclosure, a "catalyst" or "catalyst system" refers to any substance which increases the rate of a specific chemical reaction. Catalysts and catalyst systems described in this disclosure may be utilized to promote various reactions, such as, but not limited to, dehydrogenation. However, it should be understood that, according to some embodiments described herein, the disclosed catalyst systems may have other catalytic functionality and may be utilized in processes other than dehydrogenation of hydrocarbons. Accordingly, while the catalyst systems presently described may sometimes be referred to as dehydrogenation catalyst systems, they are not necessarily limited to hydrocarbon dehydrogenation functionality and may be utilized in other processes or in other materials as desired.

According to one or more embodiments, the catalyst system may comprise a zincosilicate support, one or more alkali or alkaline earth metals, and one or more platinum group metals. The zincosilicate support may be a zeolitic material comprising a microporous structure comprising pores having a diameter of less than 2 nm. According to one or more embodiments, the zincosilicate may serve as the catalyst support, and the one or more alkali or alkaline earth metals, and one or more platinum group metals may be attached to the zincosilicate support. For example, the alkali or alkaline earth metal may be attached to the zincosilicate support by ion-exchanging of the alkali or alkaline earth metal with another material of the zincosilicate support material, such a sodium, hydrogen protons, or ammonia ions. According to one or more embodiments, the platinum group metal may be incorporated into the dehydrogenation catalyst system in particle form by a method such as impregnation.

As previously disclosed, the zincosilicate support may be a zeolite. As used throughout this disclosure, a "zeolite" refers to micropore-containing (that is, comprising pores of 2 nm or less in diameter) inorganic material with regular intra-crystalline cavities and channels of molecular dimension defined by one or more framework structures. The microporous structure of zeolites (for example, 0.3 nm to 1 nm pore size) may render large surface areas and desirable size-/shape-selectivity, which may be advantageous for catalysis. The zincosilicate materials presently described may include such repeated, microporous structures.

As described in this disclosure, "zincosilicates" refer to materials consisting primarily of zinc, silicon, and oxygen atoms. The zincosilicates of the present disclosure may include zinc, silicon, and oxygen atoms in a zeolitic framework structure. Generally, the zinc and silica atoms may be connected to one another via oxygen atoms, forming repeating tetrahedrally coordinated atomic geometries. According to one or more embodiments, the zincosilicate material my comprise at least 95 percent by weight (wt. %), at least 99 wt. %, at least 99.5 wt. %, at least 99.9 wt. %, or even at least 99.99 wt. % of silicon, zinc, and oxygen (in combination) in its framework structure. As described in this disclosure, the zincosilicate incorporates at least silicon and zinc (and in some embodiments only silicon and zinc in addition to oxygen) in its microporous framework structure. It should be understood that other materials may be present in or on the zincosilicate material, but these other materials may generally be exclusive of the framework structure.

According to one or more embodiments, the zincosilicate material may comprise an MFI framework type structure (sometimes referred to as ZSM-5 framework type structure). A framework type, such as MFI framework type, may be identified by analysis techniques such as powder x-ray diffraction and comparison with known framework type's x-ray patterns, as well as Fourier transform infrared (FTIR) spectroscopy. Zeolitic framework types, such as the MFI framework type, are disclosed in "Atlas of Zeolite Framework Types, Fifth Edition" by Baerlcher, Meier, and Olson, the contents of which are incorporated by reference in their entirety.

The molar ratio of zinc atoms to silicon atoms utilized in the formation of the zincosilicate, and present in the formed zincosilicate, may be from 1:30 to 1:5, such as from 1:30 to 1:25, from 1:25 to 1:20, from 1:20 to 1:15, from 1:15 to 1:10, from 1:10 to 1:5, or any combination thereof. For example, in one embodiment, the ratio may be from 1:13 to 1:17, such as approximately 1:15. In additional embodiments, the dehydrogenation catalyst may comprise from 1 wt. % to 4 wt. % of zinc (such as from 1 wt. % to 1.5 wt. %, from 1.5 wt. % to 2 wt. %, from 2 wt. % to 2.5 wt. %, from 2.5 wt. % to 3 wt. %, from 3 wt. % to 3.5 wt. %, from 3.5 wt. % to 4 wt. %, or any combination thereof).

The dehydrogenation catalyst system may also include one or more platinum group metals that may be used as a catalytic material. Suitable platinum group metals may include Ruthenium (Ru), Rhodium (Rh), Palladium (Pd), Iridium (Ir), and Platinum (Pt). In some embodiments, only a single platinum group metal (such as Pt) is present in the dehydrogenation catalyst. In additional embodiments, two or even more different platinum group metals may be present in combination. The platinum group metal or metals may be loaded such that they are dispersed relatively evenly over the surface of the zincosilicate support, such as through incorporation by, for example, ion-exchange or impregnation. According to one or more embodiments, Pt is the only platinum group metal utilized in the dehydrogenation catalyst. In additional embodiments, at least 90 wt. %, at least 95 wt. %, or even at least 99 wt. % of the platinum group materials of the catalyst system are platinum.

According to one or more embodiments, the dehydrogenation catalyst system may comprise the one or more platinum group metals in an amount of 0.1 wt. % to 1 wt. % of the total dehydrogenation catalyst system. For example, the dehydrogenation catalyst system may comprise the one or more platinum group metals in a total amount of from 0.1 wt. % to 0.2 wt. %, from 0.2 wt. % to 0.3 wt. %, from 0.3 wt. % to 0.4 wt. %, from 0.4 wt. % to 0.5 wt. %, from 0.5 wt. % to 0.6 wt. %, from 0.6 wt. % to 0.7 wt. %, from 0.7 wt. % to 0.8 wt. %, from 0.8 wt. % to 0.9 wt. %, from 0.9 wt. % to 1 wt. %, or any combination thereof, of the total dehydrogenation catalyst system. The platinum group metal or metals may be present in elemental form, and the above described weight percentages may be indicative of weight percent of one or more platinum group metals in elemental form in combination. According to additional embodiments, the dehydrogenation catalyst may comprise the above described weight percentages of only one of Ru, Rh, Pd, Ir, or Pt (that is, where only one of Ru, Rh, Pd, Ir, or Pt is present in the dehydrogenation catalyst). For example, the dehydrogenation catalyst system may comprise from 0.1 wt. % to 1 wt. % of elemental Pt (such as in an amount of from 0.1 wt. % to 0.2 wt. %, from 0.2 wt. % to 0.3 wt. %, from 0.3 wt. % to 0.4 wt. %, from 0.4 wt. % to 0.5 wt. %, from 0.5 wt. % to 0.6 wt. %, from 0.6 wt. % to 0.7 wt. %, from 0.7 wt. % to 0.8 wt. %, from 0.8 wt. % to 0.9 wt. %, from 0.9 wt. % to 1 wt. %, or any combination thereof, of the total dehydrogenation catalyst system). In additional embodiments, the weight percentages described above are indicative of the combination of two or more of Ru, Rh, Pd, Ir, and Pt.

The dehydrogenation catalyst may additionally include one or more alkali or alkaline earth group metals. Suitable alkali or alkaline earth group metals may include Lithium (Li), Sodium (Na), Potassium (K), Rubidium (Rb), Cesium (Cs), Magnesium (Mg), and Calcium (Ca). In some embodiments, only a single alkali or alkaline earth group metal is present in the dehydrogenation catalyst. In additional embodiments, two or even more different alkali or alkaline earth elements may be present. The alkali or alkaline earth metal or metals may be loaded such that they are dispersed relatively evenly over the surface of the zincosilicate support, such as through incorporation by ion-exchange. According to one or more embodiments, Na is the only alkali or alkaline earth metal utilized in the dehydrogenation catalyst system. According to one or more additional embodiments, K is the only alkali or alkaline earth metal utilized in the dehydrogenation catalyst system. According to one or more additional embodiments, Cs is the only alkali or alkaline earth metal utilized in the dehydrogenation catalyst system.

According to one or more embodiments, the dehydrogenation catalyst system may comprise the one or more alkali or alkaline earth metals in an amount of from 0.1 wt. % to 3 wt. % of the total dehydrogenation catalyst system. For example, the dehydrogenation catalyst system may comprise the one or more alkali or alkaline earth metals in an amount of from 0.1 wt. % to 0.5 wt. %, from 0.5 wt. % to 1 wt. %, from 1 wt. % to 1.5 wt. %, from 1.5 wt. % to 2 wt. %, from 2 wt. % to 2.5 wt. %, from 2.5 wt. % to 3 wt. %, or any combination thereof, of the total dehydrogenation catalyst system. The alkali or alkaline earth group metal or metals may be present in elemental form, and the above described weight percentages may be indicative of weight percent of one or more alkali or alkaline earth group metals in elemental form. According to additional embodiments, the dehydrogenation catalyst system may comprise the above described weight percentages of only one of Li, Na, K, Rb, Cs, Mg, and Ca (that is, where only one of Li, Na, K, Rb, Cs, Mg, and Ca is introduced into the dehydrogenation catalyst system). For example, the dehydrogenation catalyst may comprise from 0.1 wt. % to 3 wt. % of elemental Na. In additional embodiments, the dehydrogenation catalyst may comprise from 0.1 wt. % to 3 wt. % of elemental K. In yet additional embodiments, the dehydrogenation catalyst may comprise from 0.1 wt. % to 3 wt. % of elemental Cs. In additional embodiments, the weight percentages described above are indicative of the combination of two or more of Li, Na, K, Rb, Cs, Mg, and Ca. Any single alkali or alkaline earth element may be present in an amount of from 0.1 wt. % to 0.5 wt. %, from 0.5 wt. % to 1 wt. %, from 1 wt. % to 1.5 wt. %, from 1.5 wt. % to 2 wt. %, from 2 wt. % to 2.5 wt. %, from 2.5 wt. % to 3 wt. %, or any combination thereof, of the total dehydrogenation catalyst system.

Without being bound by theory, it is believed that the incorporation of the alkali or alkaline earth metal may enhance the conversion, the selectivity, or both, of the dehydrogenation catalyst system for converting normal alkanes to normal alkenes. With the addition of the alkali or alkaline earth metal or metals, the risk of side reactions such as cracking, isomerization, or oligomerization as a result of the acidic nature of some conventional catalysts may be minimized.

Additionally, and still without being bound by any particular theory, it is believed that relatively heavy alkali metals such as K and Cs may provide enhanced selectivity for normal alkane dehydrogenation because of their lower tendency to acquire mobility than lithium or sodium under hydrothermal conditions prevalent during drying, regeneration thermal treatments, or reaction in the presence of steam as diluent. In particular, it is believed that these hydrothermal processes may promote the formation of hydrates of the alkali or alkaline earth metal, and that relatively heavier metals such as potassium or cesium may be less likely to form hydrates.

According to one or more embodiments, the catalyst systems described herein may be produced by a method that includes introducing one or more alkali or alkaline earth metals and introducing one or more platinum group metals to a zincosilicate support. As described herein, introducing a material to the zincosilicate support may include contacting the material with the zincosilicate support such that a portion of the material becomes integrated and attached to the zincosilicate support. As described previously in this disclosure, the zincosilicate support may comprise an MFI framework type structure incorporating at least silicon and zinc. In some embodiments, the zincosilicate support material is produced from a silicon precursor material and a zinc precursor material, where the precursor materials are mixed and crystalized to form the zeolitic zincosilicate support material.

According to one or more embodiments, the presently disclosed zincosilicate materials may be produced by a method comprising combining at least a silicon precursor material, a zinc precursor material, and a solvent to form a precursor mixture. In an additional step, the precursor mixture may be crystalized to form the zincosilicate support material. For example, a hydrogel precursor mixture may be formed which comprises water, the zinc precursor material, and the silicon precursor material. Contents of the hydrogel may then be crystalized.

The zinc precursor may be any soluble source of zinc. The zinc precursor added during preparation of the precursor mixture (such as a hydrogel) may be, for example, either a salt or complex of zinc. For example, the zinc precursor may comprise zinc sulfate. Under the synthesis conditions, a majority of the zinc may be incorporated into the framework of the zincosilicate material which, notwithstanding the zinc, may have a silicalite structure.

The silicon precursor material may be any soluble source of silicon, such as a source of silica. The sources of silica may include, for example, sodium silicate, silica hydrosol, silica gel, silica sol and silicic acid. In one embodiment, the source of silica may be an aqueous colloidal dispersion of silica particles such as the commercially available LUDOX colloidal silica commercially available from Du Pont.

The precursor mixture may additionally include a structure directing agent, such as an organic nitrogen-containing structure directing agent. The organic nitrogen-containing compound may be an amine, such as diethylamine or 1,6-diaminohexane, an alkanolamine, such as diethanolamine, or a tetraalkyl ammonium compound, such as tetrapropylammonium hydroxide (TPAOH). For example, the structure directing agent may be a quaternary cation such as tetrapropylammonium hydroxide. The structure directing agent is not particularly limited in composition, but serves to aid in the formation of the microporous, zeolitic structure of the zincosilicate. The hydrogel precursor solution may be crystallized by exposing the precursor solution to elevated temperatures. The catalyst system may then be prepared by loading the crystalline zincosilicate support with the alkali or alkaline earth metal and the one or more platinum group metals.

According to embodiments for preparing the zincosilicate, the amount of silica in the precursor solution may be from 13 to 50 moles of silica per mole of the structure directing agent. The molar ratio of solvent (such as water) to structure directing agent may be from 150:1 to 700:1. Mineralizing agents, such as sodium hydroxide, may be added to the precursor hydrogel. Crystallization may, without limitation, be carried out at a temperature in the range from 140 degrees Celsius (° C.) to 220° C. The pressure may be autogenous such that the pressure is generated within a closed vessel at the temperature employed. In some embodiments, within the selected temperature range the crystallization period may be from 1 to 4 days. The zincosilicate material may then be recovered by filtration or centrifugation, and may be washed with water at temperature such as in the range of from 15° C. to 95° C.

Without being bound by theory, it is believed that structure directing agents such as TPAOH may also act as a counter ion in the hydrogel stage as well as a counter ion to the substituted Zn ion in the solid phase. Substances such as NaOH may act as mineralizing agents in the hydrogel stage and only a small portion of the total added amount of Na ends up also as counter ion to substituted Zn in the solid phase, while the rest of the sodium remain in the mother liquor and is filtered out or washed away during the initial washing stage. It is believed that the solid product obtained is mainly TPAOH-Zeolite with small amounts of Na-Zeolite. This is evident from the catalytic testing data of the calcined samples. It should be understood that ion-exchange of the ammonium nitrate may not be necessary in the presently described embodiments.

According to one or more embodiments, the alkali or alkaline earth metal or metals, and the platinum group metal or metals, may be introduced to the zincosilicate support by any suitable technique. Such techniques for introduction may include impregnation, precipitation, ion-exchange, gelation, or any combinations thereof. In one embodiment, the zincosilicate support may be ion-exchanged with a soluble, thermally decomposable compound of alkali or alkaline earth metal together with a soluble, thermally decomposable compound of a platinum group metal. By such an incorporation technique, the platinum group metal or metals and the alkali or alkaline earth metal or metals are introduced to the support simultaneously in a single step.

In other embodiments, the one or more alkali or alkaline earth metals and the one or more platinum group metals are introduced to a zincosilicate support material at different times. For example, in one or more embodiments, the platinum group metal may be introduced separately from the alkali or alkaline earth material by impregnation after loading the zincosilicate support with alkali or alkaline earth metal via ion-exchange. In such embodiments, the process may comprise ion-exchanging the zincosilicate support with an alkali or alkaline earth metal-containing solution, filtering and drying the resultant material, then impregnating the support with a source of a platinum group metal-containing solution, and then calcining the support material that has been introduced to the alkali or alkaline earth material and the platinum group material to from the disclosed catalyst system.

According to one or more embodiments, a platinum group metal may be added in the form of a salt or complex, such as tetrammineplatinum di-hydroxide, di-nitrate or di-halide, for example dichloride. Additionally, alkali metals such as sodium, potassium or cesium may be added in the form of a salt of nitrates, nitrites, sulfates, or halides, such as for example chlorides.

The catalyst composition may be activated by a thermal treatment for the purpose of decomposing thermally decomposable compounds. The thermal treatment may be carried out in the presence of an inert gas, such as nitrogen, or an oxygen containing gas such as air. Alternatively, or in addition, the catalyst may be reductively activated by heating in the presence of a reducing gas such as hydrogen.

According to additional embodiments of the present disclosure, hydrocarbons such as alkanes may be dehydrogenated by contacting the hydrocarbons with the catalyst systems described in this disclosure. The reaction may be a batch or continuous reaction in a reactor. As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors.

According to embodiments, a variety of feed materials (sometimes referred to as reactant materials herein) may be suitable for dehydrogenation by the presently disclosed catalyst systems. Suitable dehydrogenatable hydrocarbons include paraffins, alkylaromatics, naphthenes, and olefins, which may have from 2 to 30, or even more carbon atoms. According to one or more embodiments, the reactant hydrocarbons which can be dehydrogenated with the presently disclosed catalyst systems comprise normal (that is, straight chained) paraffins or olefins having from 2 to 30, or even more carbon atoms. According to one or more embodiments presently disclosed, the catalyst systems may be particularly useful for dehydrogenating normal paraffins having from 3 to 6 carbon atoms to the corresponding linear (straight-chain) mono-olefins. According to additional embodiments, the catalyst systems may be useful for dehydrogenating paraffins having from 3 to 6 carbon atoms to the corresponding linear di-olefins. According to yet additional embodiments, the catalyst systems may be useful for dehydrogenating mono-olefins having 4 to 6 carbon atoms to the corresponding linear di-olefins.

According to one or more embodiments, alkane dehydrogenation conditions utilized for the presently described reactions may include a reaction temperature ranging from about 300° C. to 800° C. and a pressure in the range from 0.01 bar to 10 bar. For example, the reaction temperature may range from 300° C. to 400° C., from 400° C. to 500° C., from 500° C. to 600° C., from 600° C. to 700° C., from 700° C. to 800° C., or any combination thereof. The reaction pressure may range from 0.1 bar to 2 bar, from 2 bar to 4 bar, from 4 bar to 6 bar, from 6 bar to 8 bar, from 8 bar to 10 bar, or any combination thereof. Without being bound by any particular theory, it is believed that since the dehydrogenation of hydrocarbons is an endothermic reaction and conversion levels are limited by chemical equilibrium, it may be desirable to operate at relatively high temperatures and relatively low hydrogen partial pressures in order to achieve greater conversion. However, for reactions under severe conditions it may be difficult to maintain high activity and selectivity for long periods of time because undesirable side reactions such as aromatization, cracking, isomerization, coke formation, or combinations thereof, may increase. Therefore, reaction conditions may be selected with regard to maximizing one or more of catalytic activity, catalytic selectivity, and catalyst stability.

According to one or more embodiments presently described, the catalyst systems may have one or more of relatively high activity for the conversion of the previously described reactant chemical species, relatively high selectivity conversion to straight-chained alkenes, and relatively good stability. As described presently, activity is a measure of a catalyst's ability to convert reactant materials into products (substances with different chemical compositions from the reactant materials) at a specified temperature, pressure, contact time, and presence of diluents such as hydrogen, steam or nitrogen, if any. Additionally, as presently described, selectivity is a measure of the amount of a particular species in the product, in mole percent, relative to the total moles of the reactant converted. As presently described, catalyst stability is a measure of the rate of change with time of the activity and selectivity parameters, where the smaller the rate change the more stable the catalyst systems.

According to one or more embodiments, selectivity for olefin production may be achieved by the reduction in undesirable reactions such as cracking side reactions and isomerization, which may be enhanced by relatively high temperatures and low hydrogen pressures. For selective dehydrogenation processes presently described, it may be desirable to dehydrogenate normal hydrocarbon feedstocks to produce linear alkenes with little or no simultaneous cracking or isomerization reactions, which tend to produce smaller or branched hydrocarbon chains, respectively. According to one or more embodiments, the isomerization or cracking activity of the presently described dehydrogenation reactions may be maintained at less than 2 mol. % of the feedstock, measured as the number of moles of isomerized or cracked hydrocarbons in the product relative to the feedstock.

In one or more embodiments, a feed stream may be introduced into a reactor which contains the dehydrogenation catalyst system. The feed stream may comprise the reactant material (for example, normal alkanes) as well as a diluent component. Diluent materials may include hydrogen, steam, methane, inert gases such as argon or nitrogen, or combinations thereof. Without limitation, the weight ratio of diluent to reactant material may be from 500 to 5000, such as from 500 to 1000, from 1000 to 2000, from 2000 to 3000, from 3000 to 4000, from 4000 to 5000, or any combination thereof.

The product stream exiting the reactor may comprise dehydrogenated hydrocarbons, unconverted dehydrogenatable hydrocarbons (identical to the reactant material), and the diluent material. Diluent gases, such as hydrogen may be separated from the other portions of the product stream. These diluent gases may be recycled to be used again as diluent materials, or may be utilized in other chemical processes. The dehydrogenated hydrocarbons and unconverted dehydrogenatable hydrocarbons may be separated by downstream separation processes as desired. In some embodiments, the unconverted hydrocarbons may then be recycled to the process for subsequent reaction passes.

According to one or more embodiments, the presently described catalyst systems may be utilized to convert n-pentane to at least n-pentenes (1-pentene, cis-2-pentene, and trans-2-pentene). In such embodiments, the presently described catalysts may have a selectivity for n-pentene conversion from n-pentane of at least 30 mol. % (such as at least 35 mol. %, at least 40 mol. %, at least 45 mol. %, at least 50 mol. %, at least 55 mol. %, at least 60 mol. %, at least 65 mol. %, at least 70 mol. %, at least 75 mol. %, at least 80 mol. %, or even at least 85 mol. %). Conventional catalysts may only have selectivity of less than 30 mol. %. For the presently described catalyst systems, the total yield of n-pentenes from n-pentane may be at least 20 mol. % (such as at least 25 mol. %, at least 30 mol. %, or even at least 35 mol. %). Conventional catalysts may only have n-pentene product yields of less than 20 mol. %.

In one or more embodiments, the diluent material in the feed stream may comprise from 5 vol. % to 30 vol. % hydrogen. For example, from 5 vol. % to 10 vol. %, from 10 vol. % to 15 vol. %, from 15 vol. % to 20 vol. %, from 20 vol. % to 25 vol. %, from 25 vol. % to 30 vol. %, or any combination thereof of hydrogen gas may be utilized in the diluent. In some embodiments, this ratio of hydrogen to other diluents may be utilized for the dehydrogenation of C4 to C6 hydrocarbons. In some embodiments, the diluent may include, or consist entirely of hydrogen and an inert has, such as nitrogen. Without being bound by any particular theory, it is believed that this ratio of hydrogen as a diluent increases selectivity for normal alkenes and normal alkene yield under some reaction conditions. Catalyst stability may also be increased with the use of 5 vol. % to 30 vol. % of hydrogen as diluent.

In view of the present disclosure, it should now be understood that zincosilicate supported catalyst systems which additional comprise alkali or alkaline earth metal additives and platinum group metal catalysts may be utilized for the dehydrogenation of hydrocarbons, such as the conversion of n-alkanes to n-alkenes. Such catalyst systems may have enhanced selectivity for n-alkene conversion.

EXAMPLES

Using the catalyst systems and methods of the present disclosure, catalyst systems were produced which exemplify the catalytic attributes presently described. It should be understood that the ensuing examples are illustrative of one or more embodiments presently disclosed, and should not be construed as in any way as limiting on the appended claims or other portions of the present application.

Example 1—Preparation of Zincosilicate

Zincosilicate, which was utilized as a support material in the catalyst systems prepared in the subsequent examples, was prepared according to the process presently disclosed.

To prepare a sample of zincosilicate, 36 grams of zinc sulfate (ZnSO$_4$·7H$_2$O) were dissolved in 120 grams of deionized water to form a first mixture. Aqueous ammonia solution (25 vol. %) was added dropwise with stirring to the first mixture until the pH reached 6, forming a precipitate. The precipitate was filtered, washed with deionized water, and dried on a Buchner filter until dry after about 6 hours. Then, 16 grams of sodium hydroxide was mixed with the formed precipitate along with 160 grams of deionized water, which was stirred for 3 hours. Then, 200 grams of tetrapropylammonium hydroxide (TPAOH) aqueous solution (containing 20 wt. % TPAOH) was added and the mixture was stirred for another 8 hours. 280 grams of LUDOX AS40 (commercially available from DuPont and containing 40 wt. % silica (SiO$_2$)) was then added to the mixture under vigorous stirring and the mixture was stirred for 12 hours to form a hydrogel. The formed hydrogel had a molar ratio of 1.6 Na$_2$O:1.57 TPAOH:ZnO:14.9 SiO$_2$:217 H$_2$O.

The hydrogel was loaded into an approximately 0.25 liter pressure vessel, aged at room temperature for 24 hours, and then heated at 175° C. for 4 days (without stirring). At the end of this period, the pressure vessel was cooled to ambient temperature and the contents were filtered, washed, and dried at 100° C. The zinc content in the resulting zincosilicate product was found to be 3 wt. %.

Figure 1:
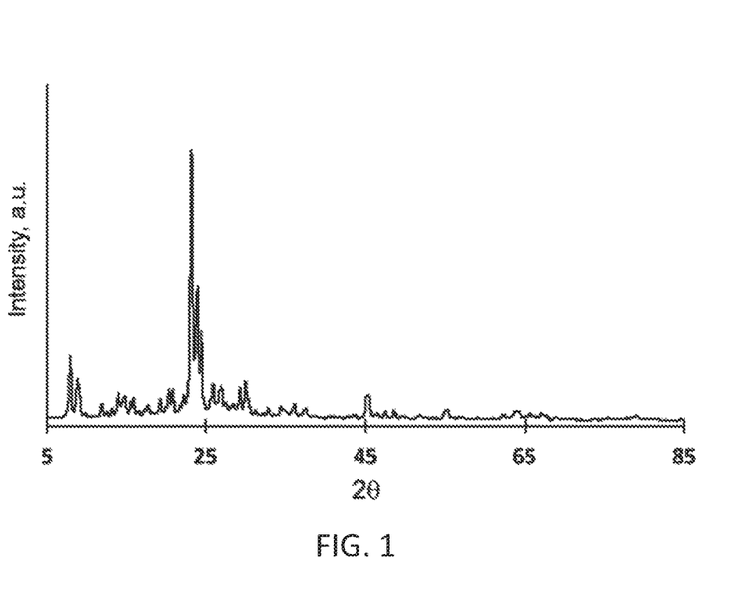
FIG. 1 graphically depicts the X-ray powder diffraction pattern of an MFI framework type zincosilicate support structure, according to one or more embodiments presently disclosed.
Figure 2:
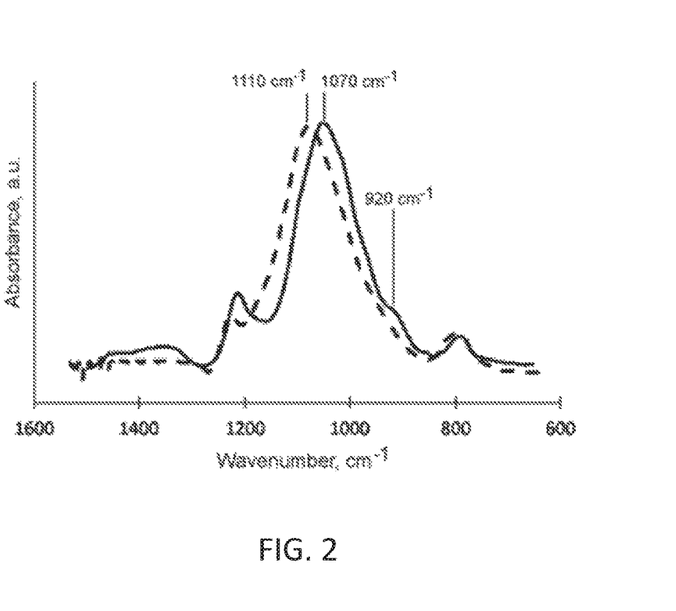
FIG. 2 graphically depicts a Fourier transform infrared (FTIR) spectroscopy reading of an MFI framework type zincosilicate support structure, according to one or more embodiments presently disclosed.

When compared to the reference International Centre for Diffraction Data (ICDD) database card no. 04-007-735, the X-ray powder diffraction of the dried product was found to be that of a silicalite-1 (MFI-type) structure. The X-ray powder diffraction analysis is depicted in FIG. 1. Substitution of Zn$^{2+}$ cation within the oxygen framework of the MFI structure was substantiated by FTIR spectroscopy, which showed a shoulder at around 920 cm$^{-1}$ in the infrared (IR) spectra of zincosilicate. The results of the FTIR spectroscopy are depicted in FIG. 2 (shown as the solid line). The IR band observed at 910-950 inverse centimeters (cm$^{-1}$) is associated with asymmetric stretching vibration of the Si—O—Zn group from the possible substitution of heteroatom (Zn) in the Si—O—Si units. Moreover, FIG. 2 depicts a comparative silicalite FTIR spectra (shown in dashed line), showing that there is a clear shift of the wavenumber of the Si—O—Si lattice vibration 1110 cm$^{-1}$ towards lower values due to the incorporation of the zinc heteroatom into the MFI framework in the zincosilicate samples.

The dried zincosilicate sample was then calcined by heating at a rate of 1.5 degrees Celsius per minute (° C./min) to 550° C. in air and maintained at 550° C. for at least 18 hours to remove the organic content.

Comparative Example A—Preparation of Pt/Zincosilicate Catalyst

To form a conventional catalyst system, referred to as "Catalyst A", 15 grams of the zincosilicate of Example 1 was mixed with 12 grams of deionized water and 0.225 gram of tetraammoneplatinum(II) nitrate (Pt)NH$_3$)$_4$(NO$_3$)$_2$), and the mixture was subsequently stirred and then dried in an oven at 100° C. for 24 hours. The dried material sample was calcined at 400° C. for 18 hours in air.

Example 2—Preparation of Pt—Na/Zincosilicate Catalyst

To form another catalyst, referred to as "Catalyst B", 15 grams of calcined zincosilicate prepared in Example 1 was exchanged with a 200 milliliter solution of mixed sodium nitrate NaNO$_3$ (0.5 M) and Pt(NH$_3$)$_4$(NO$_3$)$_2$ (11.5 millimolar (mM)) for 8 hours at 85° C. The Na and Pt exchanged zincosilicate was filtered, washed with deionized water, dried at 100° C. for 24 hours, and calcined at 400° C. for 18 hours in air. The Pt content in the sample was 0.45 wt. % and the Na content was 0.58 wt. %.

Example 3—Catalyst Activation and Testing

Catalysts A and B (of Comparative Example A and Example 2, respectively) were activated in the reactor before testing. The catalysts were pressed at 8 tones pressure to form tablets and crushed and sieved to form 200 to 500 micrometer granules. The granules (approx. 1.5 cubic centimeters (cm$^3$), 0.75 grams) were packed into a tubular Hastelloy-X reactor which was 310 millimeters (mm) in length and had a 9.1 mm internal diameter. The reactor had a thermocouple immersed into the catalyst bed.

Air (approximately 100 cubic centimeters per minute (cm$^3$/min)) was passed over the catalyst systems and the temperature was raised to 400° C. at the rate of 1.5 degrees Celsius per minute (° C./min) and kept at 400° C. for at least 4 hours. The catalyst system was then flushed with nitrogen (approximately 100 cm$^3$/min) for 30 minutes and hydrogen was then passed at 100 cm$^3$/min for 4 hours. The temperature was then raised to the reaction temperature at a rate of 1.5° C./min.

The activated catalyst systems as described were tested for the dehydrogenation of propane and n-pentane in a continuous flow reactor. The results obtained and conditions used are given in the Tables 1, 2, and 3.

Table 1 shows the reaction results obtained using n-pentane feedstock over catalyst A. Each activity value listed was measured after 12 hours on stream, which reflects the relatively high stability of the catalyst with time. In this case a total of 100 ml/min diluting carrier gas mixture of hydrogen and nitrogen was used. The composition of the carrier gas was varied step-wise by 15 milliliter per minute (ml/min) from pure hydrogen gas to pure nitrogen gas. It can be seen that n-pentane conversion over Catalyst A of Comparative Example A is found to increase in the presence of some hydrogen gas in the feed stream, where it is a maximum when the hydrogen content in the feed stream is 40 ml/min. In addition to its dehydrogenation activity producing normal pentenes (1-pentene, cis-2-pentene, and trans-2-pentene), and under all compositions of carrier-diluent gas, Catalyst A exhibited significant cracking and hydrocracking activity. It also exhibited relatively high hydroisomerization and isomerization activity producing isopentane and isopentenes (3-methyl-1-butene, 2-methyl-1-butene, and 2-methyl-2-butene), respectively, with higher selectivity than for the formation of linear dehydrogenation products.

It is noted that testing of Catalyst A was carried out at 525° C., where each measurement is reported after 12 hours on stream, under atmospheric pressure, liquid n-pentane flow 0.04 ml/min, and weight hourly space velocity (WHSV) of 2 per hour (1/h). Additionally, it is noted that in Table 1, "conversion" refers to n-pentane conversion; "n-pentenes" refers to the combination of 1-pentene, cis-2-pentene, and trans-2-pentene; "pentadienes" refers to the combination of 1,4-pentadiene, (Z)-1,3-pentadiene, and (E)-1,3-pentadiene; "isopentenes" refers to the combination of 3-methyl-1-butene, 2-methyl-1-butene, and 2-methyl-2-butene; "cracking products" refers to hydrocracking and cracking products such as methane, ethane, ethylene, propane, propylene, n-butane, 2-trans-butene, 1-butene, and 2-cis-butene; and "n-Pentene yield" refers to n-pentene yield including 1-pentene, cis-2-pentene, trans-2-pentene.

TABLE 1

| H₂, ml/min | N₂, ml/min | Conversion, mol. % | Selectvity, mol. % | | | | | n-Pentene Yield, mol. % |
|---|---|---|---|---|---|---|---|---|
| | | | n-Pentenes | Pentadienes | Iso-pentenes | Iso-pentane | Cracking Products | |
| 100 | 0 | 63.4 | 14.9 | 2.3 | 22.5 | 47.0 | 11.4 | 9.4 |
| 85 | 15 | 64.1 | 15.8 | 2.8 | 23.9 | 44.9 | 10.9 | 10.1 |
| 70 | 30 | 67.9 | 15.7 | 4.0 | 25.8 | 41.2 | 11.6 | 10.6 |
| 55 | 45 | 68.1 | 18.9 | 5.4 | 30.5 | 34.7 | 9.5 | 12.9 |
| 40 | 60 | 69.9 | 20.9 | 7.9 | 34.8 | 27.3 | 8.9 | 14.6 |
| 25 | 75 | 65.4 | 25.5 | 12.5 | 41.4 | 14.3 | 7.6 | 16.7 |
| 10 | 90 | 52.0 | 26.5 | 21.6 | 40.5 | 7.2 | 7.2 | 13.8 |
| 0 | 100 | 41.1 | 22.5 | 40.7 | 28.6 | 5.3 | 6.2 | 9.3 |

Table 2 shows the reaction results obtained using n-pentane feedstock over Catalyst B of Example 2. Each of the activity values listed was measured after 12 hours on stream which reflects the relatively high stability of the catalyst with time. In this case a total of 100 ml/min diluting carrier gas mixture of hydrogen and nitrogen was used. The composition of the carrier gas was varied step-wise by 15 ml/min from pure hydrogen gas to pure nitrogen gas. It can be seen that n-pentane conversion over Catalyst B and its selectivity for normal pentenes at 525° C. are affect by the presence of hydrogen gas in the feed stream. n-pentane conversion and selectivity for normal pentenes in the product reached a maximum value of 62.1% and 62.5%, respectively, when the hydrogen content in the feed stream was 10 ml/min. It is noticed that under all compositions of diluent carrier gas used, Catalyst B exhibited a much higher combined selectivity for normal pentenes and pentadienes (1,4-Pentadiene, (Z)-1,3-Pentadiene, (E)-1,3-Pentadiene) than that observed over Catalyst A, and a greater yield for normal pentenes reaching a maximum of 38.2%.

It is noted that testing of Catalyst B as shown in Table 2 was carried out at 525° C., where each measurement is reported after 12 hours on stream, under atmospheric pressure, liquid n-pentane flow 0.04 ml/min, and WHSV of 2/h. Additionally, it is noted that in Table 2, "conversion" refers to n-pentane conversion; "n-pentenes" refers to the combination of 1-pentene, cis-2-pentene, and trans-2-pentene; "pentadienes" refers to the combination of 1,4-pentadiene, (Z)-1,3-pentadiene, and (E)-1,3-pentadiene; "isopentenes" refers to the combination of 3-methyl-1-butene, 2-methyl-1-butene, and 2-methyl-2-butene; and "yield" refers to n-pentene yield including 1-pentene, cis-2-pentene, trans-2-pentene.

TABLE 2

| H₂, ml/min | N₂, ml/min | Conversion, mol. % | Selectivity, mol. % | | | Yield, mol. % |
|---|---|---|---|---|---|---|
| | | | n-Pentenes | Pentadienes | Isopentenes | n-Pentenes |
| 100 | 0 | 34.9 | 48.0 | 5.3 | 7.6 | 16.7 |
| 85 | 15 | 37.0 | 50.8 | 6.7 | 8.1 | 18.8 |
| 70 | 30 | 39.0 | 52.1 | 8.7 | 8.4 | 20.4 |
| 55 | 45 | 45.6 | 55.1 | 11.4 | 9.6 | 25.1 |
| 40 | 60 | 50.7 | 57.3 | 15.6 | 9.7 | 29.1 |
| 25 | 75 | 56.0 | 61.5 | 21.4 | 7.6 | 34.4 |
| 10 | 90 | 62.1 | 61.5 | 30.2 | 4.6 | 38.2 |
| 0 | 100 | 63.4 | 40.9 | 54.0 | 2.5 | 26.0 |

Table 3 shows the results obtained using propane feedstock over Catalyst B at different nitrogen dilution levels and reaction temperatures. Each listed activity value was measured after 12 hours on stream which reflects the relatively high stability of the catalyst with time. It is also found that both propane conversion and selectivity to propylene increase with increasing dilution levels, while lower reaction temperatures lead to further improvement in the selectivity for propylene production but with a concurrent decrease in propane conversion rates. It is noted that testing of Catalyst B shown in Table 3 was carried out under atmospheric pressure and WHSV of 2/h.

TABLE 3

| Propane, flow ml/min | Nitrogen, flow ml/min | Temperature, ° C. | Propane, mol. % conversion | Propylene, mol. % selectivity |
|---|---|---|---|---|
| 17 | 0 | 575 | 38.5 | 87.4 |
| 17 | 10 | 575 | 49.3 | 93.9 |
| 17 | 23 | 575 | 60.5 | 94.7 |
| 17 | 53 | 575 | 66.1 | 94.5 |
| 17 | 83 | 575 | 67.8 | 96.6 |
| 17 | 83 | 550 | 53.6 | 98.6 |
| 17 | 83 | 525 | 44.0 | 98.8 |

Example 4—Preparation of Another Pt—Na/Zincosilicate Catalyst

In order to further improve the catalyst's selectivity for the formation of straight-chain normal alkenes, the metal loading step used in Example 2 was divided into two parts where one part involved ion-exchange of the alkali metal and the other part involved the impregnation with the noble metal.

To form a two-step platinum and sodium impregnated catalyst, referred to as "Catalyst C", 15 grams of calcined zincosilicate prepared in Example 1 was exchanged twice with 200 milliliter solution of NaNO₃ (0.5 M) for 5 hours at room temperature. The sodium exchanged zincosilicate was filtered, washed with deionized water dried at 100° C. for 24 hours. The final Na content in the sample was 0.9 wt. %. The formed Na-zincosilicate (15 grams) was mixed with 12 grams of deionized water and 0.225 gram of Pt(NH$_3$)$_4$(NO$_3$)$_2$ and the mixture was stirred, and then dried in an oven at 100° C. for 24 hours. The dried sample was calcined at 400° C. for 18 hours in air and was found to contain 0.45 wt. % Pt.

Example 5—Preparation of Pt/K-Zincosilicate

To form a Pt and K impregnated zincosilicate catalyst, referred to as "Catalyst D", 15 grams of calcined zincosilicate prepared in Example 1 was exchanged twice with 200 milliliter solution of KNO$_3$ (0.5 M) for 5 hours at room temperature. The potassium exchanged zincosilicate was filtered, washed with deionized water, and dried at 100° C. for 24 hours. The final K content in the sample is 1.2 wt. %. The formed K-zincosilicate (15 grams) was mixed with 12 grams of deionized water and 0.225 gram of Pt(NH$_3$)$_4$(NO$_3$)$_2$ and the mixture was stirred and then dried in an oven at 100° C. for 24 hours. The dried sample was calcined at 400° C. for 18 hours in air. The sample was found to contain 0.45 wt. % Pt.

Example 6—Preparation Pt/Cs-Zincosilicate

To form a Pt and Cs impregnated zincosilicate catalyst, referred to as "Catalyst E", 15 grams of calcined zincosilicate prepared in Example 1 was exchanged twice with 200 milliliter solution of CsNO$_3$ (0.5M) for 5 hours at room temperature. The cesium exchanged zincosilicate was filtered and washed with deionized water dried at 100° C. for 24 hours. The final Cs content in the sample was 2.6 wt. %. The formed Cs-Zincosilicate (15 grams) was mixed with 12 grams of deionized water and 0.225 gram of Pt(NH$_3$)$_4$(NO$_3$)$_2$ and the mixture was stirred, and dried in an oven at 100° C. for 24 hours. The dried sample was calcined at 400° C. for 18 hours in air. The prepared catalyst was found to contain 0.45 wt. % of Pt.

Example 7—Catalyst Activation and Testing

Catalysts C, D, and E (of Examples 4, 5, and 6, respectively) were each activated in the reactor before testing. The catalysts were pressed at 8 tones pressure to form tablets and crushed and sieved to form 200 to 500 micrometer granules. The granules (approximately 1.5 cm$^3$, 0.75 grams) were packed into a tubular Hastelloy-X reactor which was 310 mm in length and 9.1 mm internal diameter. The reactor had a thermocouple immersed into the catalyst bed.

Air (approximately 100 cm$^3$/min) was passed over the catalyst and the temperature was raised to 400° C. at the rate of 1.5° C./min and kept at 400° C. for at least 4 hours. The catalyst was then flushed with nitrogen (approximately 100 cm$^3$/min) for 30 minutes and hydrogen was then passed at 100 cm$^3$/min for 4 hours. The temperature was then raised to the reaction temperature at a rate of 1.5° C./min.

The activated catalyst systems as described were tested for the dehydrogenation of n-pentane in a continuous flow reactor. Tables 4, 5 and 6 show the reaction results obtained using n-pentane feedstock over Catalysts C, D and E, respectively. Each set of activity values listed is measured after 12 hours on stream which reflects the relatively high stability of the catalyst with time. In this case a total of 100 ml/min diluting carrier gas mixture of hydrogen and nitrogen was used. The composition of the carrier gas was varied step-wise by 15 ml/min from pure hydrogen gas to pure nitrogen gas. It can be seen that the catalysts' activity and selectivity for dehydrogenation products are affected by the presence of hydrogen in the feed stream. Both conversion of n-pentane and selectivity for linear pentenes were found to increase with decreasing hydrogen content in the carrier gas mixture and decrease again when pure nitrogen is used. It was also observed that the combined selectivity for normal pentenes and pentadienes generally increase with the addition of small amounts of hydrogen in the feed stream, and reaches more than 95 mol. % at conversion levels greater than 40 mol. % over each of the three catalysts, at the reaction temperatures of 500° C. and 525° C.

It is noted that Table 4 contains data related to Catalyst C of Example 4, Table 5 contains data related to Catalyst D of Example 5, and Table 7 contains data related to Catalyst E of Example 6. In each of Tables 4-6, it is noted that "S—C Normal Pentene" refers to straight-chain normal pentenes including 1-pentene, cis-2-pentene, and trans-2-pentene; and "pentadiene" refers to the combination of 1,4-pentadiene, (Z)-1,3-pentadiene, and (E)-1,3-pentadiene. Testing reported in Tables 4-6 occurred over 0.75 wt. % of the respective catalyst under atmospheric pressure, with liquid n-pentane flow 0.04 ml/min, and WHSV of 2/h.

| | H$_2$:N$_2$ 100:0 ml/min | H$_2$:N$_2$ 85:15 ml/min | H$_2$:N$_2$ 70:30 ml/min | H$_2$:N$_2$ 55:45 ml/min | H$_2$:N$_2$ 40:60 ml/min | H$_2$:N$_2$ 25:75 ml/min | H$_2$:N$_2$ 10:90 ml/min | H$_2$:N$_2$ 0:100 ml/min |
|---|---|---|---|---|---|---|---|---|
| Temperature | | | | 500° C. | | | | |
| n-Pentane Conversion, mol. % | 16.0 | 17.4 | 19.8 | 23.1 | 28.0 | 36.6 | 41.8 | 33.2 |
| S-C Normal Pentene Selectivity, mol. % | 74.8 | 75.3 | 76.6 | 78.5 | 79.8 | 78.7 | 74.7 | 49.9 |
| S-C Normal Pentene Yield, mol. % | 12.0 | 13.1 | 15.2 | 18.1 | 22.4 | 28.8 | 31.3 | 16.6 |
| Pentadiene Selectivity, mol. % | 3.5 | 4.2 | 5.1 | 6.6 | 8.7 | 13.1 | 21.2 | 46.9 |
| Temperature | | | | 525° C. | | | | |
| n-Pentane Conversion, mol. % | 27.4 | 27.9 | 30.7 | 34.7 | 40.2 | 46.4 | 47.7 | 29.7 |

-continued

|  | H$_2$:N$_2$ 100:0 ml/min | H$_2$:N$_2$ 85:15 ml/min | H$_2$:N$_2$ 70:30 ml/min | H$_2$:N$_2$ 55:45 ml/min | H$_2$:N$_2$ 40:60 ml/min | H$_2$:N$_2$ 25:75 ml/min | H$_2$:N$_2$ 10:90 ml/min | H$_2$:N$_2$ 0:100 ml/min |
|---|---|---|---|---|---|---|---|---|
| S-C Normal Pentene Selectivity, mol. % | 66.3 | 73.9 | 75.6 | 76.5 | 75.6 | 73.7 | 63.7 | 42.3 |
| S-C Normal Pentene Yield, mol. % | 18.1 | 20.6 | 23.2 | 26.6 | 30.4 | 34.1 | 30.4 | 12.5 |
| Selectivity, mol. % | 6.6 | 7.4 | 8.8 | 11.0 | 14.1 | 19.2 | 31.9 | 54.0 |

TABLE 5

|  | H$_2$:N$_2$ 100:0 ml/min | H$_2$:N$_2$ 85:15 ml/min | H$_2$:N$_2$ 70:30 ml/min | H$_2$:N$_2$ 55:45 ml/min | H$_2$:N$_2$ 40:60 ml/min | H$_2$:N$_2$ 25:75 ml/min | H$_2$:N$_2$ 10:90 ml/min | H$_2$:N$_2$ 0:100 ml/min |
|---|---|---|---|---|---|---|---|---|
| Temperature | | | | 500° C. | | | | |
| n-Pentane Conversion, mol. % | 16.6 | 17.5 | 19.8 | 23.5 | 29.0 | 37.7 | 48.2 | 33.4 |
| S-C Normal Pentene, mol. % | 72.7 | 76.8 | 79.5 | 78.8 | 79.5 | 78.4 | 72.3 | 51.5 |
| S-C Normal Pentene Yield, mol. % | 12.1 | 13.5 | 15.7 | 18.5 | 23.0 | 29.5 | 34.9 | 17.2 |
| Selectivity, mol. % | 3.7 | 4.3 | 5.3 | 6.7 | 9.1 | 13.6 | 23.3 | 45.5 |
| Temperature | | | | 525° C. | | | | |
| n-Pentane Conversion, mol. % | 26.6 | 28.3 | 31.7 | 36.3 | 41.5 | 48.9 | 50.4 | 29.4 |
| S-C Normal Pentene Selectivity, mol. % | 73.3 | 74.9 | 76.3 | 74.2 | 75.5 | 71.7 | 63.4 | 41.0 |
| S-C Normal Pentene Yield, mol. % | 19.5 | 21.2 | 24.2 | 26.9 | 31.4 | 35.1 | 32.0 | 12.1 |
| Selectivity, mol. % | 7.1 | 8.1 | 9.7 | 12.2 | 15.3 | 21.5 | 32.4 | 55.3 |

TABLE 6

|  | H$_2$:N$_2$ 100:0 ml/min | H$_2$:N$_2$ 85:15 ml/min | H$_2$:N$_2$ 70:30 ml/min | H$_2$:N$_2$ 55:45 ml/min | H$_2$:N$_2$ 40:60 ml/min | H$_2$:N$_2$ 25:75 ml/min | H$_2$:N$_2$ 10:90 ml/min | H$_2$:N$_2$ 0:100 ml/min |
|---|---|---|---|---|---|---|---|---|
| Temperature | | | | 500° C. | | | | |
| n-Pentane Conversion, mol. % | 16.6 | 16.7 | 18.7 | 21.9 | 26.7 | 34.0 | 37.1 | 33.1 |
| S-C Normal Pentene Selectivity, mol. % | 73.1 | 82.2 | 85.4 | 85.6 | 83.6 | 78.9 | 72.4 | 55.2 |
| S-C Normal Pentene Yield, mol. % | 12.2 | 13.8 | 16.0 | 18.7 | 22.3 | 26.8 | 26.8 | 18.3 |
| Selectivity mol. % | 4.3 | 4.9 | 5.9 | 7.3 | 9.8 | 15.1 | 24.1 | 41.9 |

TABLE 6-continued

| | H$_2$:N$_2$ 100:0 ml/min | H$_2$:N$_2$ 85:15 ml/min | H$_2$:N$_2$ 70:30 ml/min | H$_2$:N$_2$ 55:45 ml/min | H$_2$:N$_2$ 40:60 ml/min | H$_2$:N$_2$ 25:75 ml/min | H$_2$:N$_2$ 10:90 ml/min | H$_2$:N$_2$ 0:100 ml/min |
|---|---|---|---|---|---|---|---|---|
| Temperature | | | | 525° C. | | | | |
| n-Pentane Conversion, mol. % | 27.1 | 28.6 | 31.6 | 36.4 | 40.1 | 44.8 | 48.6 | 38.7 |
| S-C Normal Pentene Selectivity, mol. % | 72.8 | 77.2 | 79.1 | 77.3 | 76.3 | 72.1 | 62.5 | 40.6 |
| S-C Normal Pentene Yield, mol. % | 19.7 | 22.1 | 25.0 | 28.1 | 30.6 | 32.3 | 30.4 | 15.7 |
| Selectivity, mol. % | 8.2 | 9.0 | 10.7 | 13.6 | 17.1 | 22.1 | 33.5 | 56.1 |

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated herein.

It should also be understood that embodiments described as "conventional" or "comparative" are not necessarily outside of the scope of the present claims, and that applicants are not making an admission that an embodiment was previously disclosed by referring to it as "conventional" or "comparative" in the present disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various embodiments described herein. Further, it will be apparent that modifications and variations are possible without departing from the scope of the appended claims.

Several non-limiting aspects of the disclosure are presently disclosed. According to a first aspect of the present disclosure, a catalyst system comprises a zincosilicate support material comprising an MFI framework type structure incorporating at least silicon and zinc; one or more alkali or alkaline earth metals; and one or more platinum group metals.

A second aspect of the present disclosure may include the first aspect, wherein the molar ratio of zinc to silicon in the MFI framework type structure is from 1:30 to 1:5.

A third aspect of the present disclosure may include any of the preceding aspects, wherein the zincosilicate support comprises at least 95 wt. % of silicon, zinc, and oxygen in its framework structure.

A fourth aspect of the present disclosure may include any of the preceding aspects, wherein the one or more alkali or alkaline earth metals are selected from K, Na, or Cs.

A fifth aspect of the present disclosure may include any of the preceding aspects, wherein the catalyst system comprises the alkali or alkaline earth metals in a total amount of from 0.1 wt. % to 3 wt. % of the catalyst system.

A sixth aspect of the present disclosure may include any of the preceding aspects, wherein at least a portion of the one or more alkali or alkaline earth metals are present in elemental form.

A seventh aspect of the present disclosure may include any of the preceding aspects, wherein the one or more platinum group metals are selected from Ru, Rh, Pd, Ir, or Pt.

An eighth aspect of the present disclosure may include any of the preceding aspects, wherein the catalyst system comprises the one or more platinum group metals in a total amount of from 0.1 wt. % to 1 wt. % of the catalyst system.

A ninth aspect of the present disclosure may include any of the preceding aspects, wherein at least a portion of the one or more platinum group metals are present in elemental form.

According to a tenth aspect of the present disclosure, a catalyst system may be made by a method comprising introducing one or more alkali or alkaline earth metals to a zincosilicate support material; and introducing one or more platinum group metals to the zincosilicate support material; wherein the zincosilicate support material comprises an MFI framework type structure incorporating at least silicon and zinc.

An eleventh aspect of the present disclosure may include any of the preceding aspects, wherein the one or more alkali or alkaline earth metals and the one or more platinum group metals are introduced to the zincosilicate support material simultaneously.

A twelfth aspect of the present disclosure may include any of the preceding aspects, wherein the one or more alkali or alkaline earth metals and the one or more platinum group metals are introduced to the zincosilicate support material at different times.

A thirteenth aspect of the present disclosure may include any of the preceding aspects, further comprising producing the zincosilicate support material by a method comprising: combining at least a silicon precursor material, a zinc precursor material, and a solvent to form a precursor mixture; and crystallizing the precursor mixture to form the zincosilicate support material.

A fourteenth aspect of the present disclosure may include any of the preceding aspects, wherein the solvent comprises water and the precursor mixture is a hydrogel.

A fifteenth aspect of the present disclosure may include any of the preceding aspects, further comprising calcining the zincosilicate support material following the introduction of the one or more platinum group metals and following the introduction of the one or more platinum group metals.

A sixteenth aspect of the present disclosure may include any of the preceding aspects, wherein the one or more alkali or alkaline earth metals are introduced to the zincosilicate support material by ion-exchange.

A seventeenth aspect of the present disclosure may include any of the preceding aspects, wherein the one or more platinum group metals are introduced to the zincosilicate support material by impregnation, precipitation, ion-exchange, or gelation.

An eighteenth aspect of the present disclosure may include any of the preceding aspects, wherein the precursor mixture further comprises a structure directing agent.

According to a nineteenth aspect of the present disclosure, one or more reactant hydrocarbons may be dehydrogenated by a method comprising: contacting the one or more reactant hydrocarbons with a catalyst system to dehydrogenate at least a portion of the reactant hydrocarbons, the catalyst system comprising: a zincosilicate support material comprising an MFI framework type structure incorporating at least silicon and zinc; one or more alkali or alkaline earth metals; and one or more platinum group metals.

A twentieth aspect of the present disclosure may include any of the preceding aspects, wherein the reactant hydrocarbons comprise one or more of n-butane, n-pentane, or n-hexane.

A twenty-first aspect of the present disclosure may include any of the preceding aspects, wherein the method for dehydrogenating the reactant hydrocarbons results in a selectivity of n-butene, n-pentene, or n-hexene of at least 30 mol. %.

A twenty-second aspect of the present disclosure may include any of the preceding aspects, wherein the method for dehydrogenating the reactant hydrocarbons results in a yield of n-butene, n-pentene, or n-hexane of at least 20 mol. %.

A twenty-third aspect of the present disclosure may include any of the preceding aspects, wherein the reactant hydrocarbons are mixed with a diluent, the diluent comprising hydrogen, steam, methane, argon, nitrogen, or mixtures thereof.

A twenty-fourth aspect of the present disclosure may include any of the preceding aspects, wherein the diluent comprises from 5 vol. % to 30 vol. % of hydrogen.

What is claimed is:

1. A catalyst system useful for the dehydrogenation of hydrocarbons, the catalyst system comprising:
    a zincosilicate support material comprising an MFI framework type structure incorporating at least silicon and zinc;
    one or more alkali or alkaline earth metals; and
    one or more platinum group metals.

2. The catalyst system of claim 1, wherein the molar ratio of zinc to silicon in the MFI framework type structure is from 1:30 to 1:5.

3. The catalyst system of claim 1, wherein the zincosilicate support material comprises at least 95 wt. % of silicon, zinc, and oxygen in its framework structure.

4. The catalyst system of claim 1, wherein the one or more alkali or alkaline earth metals are selected from K, Na, or Cs.

5. The catalyst system of claim 1, wherein the catalyst system comprises the alkali or alkaline earth metals in a total amount of from 0.1 wt. % to 3 wt. % of the catalyst system.

6. The catalyst system of claim 1, wherein at least a portion of the one or more alkali or alkaline earth metals are present in elemental form.

7. The catalyst system of claim 1, wherein the one or more platinum group metals are selected from Ru, Rh, Pd, Ir, or Pt.

8. The catalyst system of claim 1, wherein the catalyst system comprises the one or more platinum group metals in a total amount of from 0.1 wt. % to 1 wt. % of the catalyst system.

9. The catalyst system of claim 1, wherein at least a portion of the one or more platinum group metals are present in elemental form.

* * * * *